United States Patent
Parab

[19]

[11] Patent Number: 5,885,596
[45] Date of Patent: Mar. 23, 1999

[54] METHODS AND COMPOSITIONS FOR FINE LINES AND/OR WRINKLES

[75] Inventor: Prakash Parab, Williamsville, N.Y.

[73] Assignee: Bristol-Myers Squibb Company, New York, N.Y.

[21] Appl. No.: 899,419

[22] Filed: Jul. 23, 1997

[51] Int. Cl.⁶ .................................................. A61K 7/48
[52] U.S. Cl. .................... 424/401; 514/844; 514/845; 514/846
[58] Field of Search ............... 424/401; 514/844, 514/848, 846

[56] References Cited

U.S. PATENT DOCUMENTS

| | | | |
|---|---|---|---|
| 4,362,715 | 12/1982 | Strianse et al. | 424/78 |
| 4,474,763 | 10/1984 | Lubowe | 424/177 |
| 4,603,146 | 7/1986 | Kligman | 514/559 |
| 4,826,828 | 5/1989 | Wilmott et al. | 514/63 |
| 4,877,805 | 10/1989 | Kligman | 514/381 |
| 4,888,342 | 12/1989 | Kligman | 514/419 |
| 5,091,171 | 2/1992 | Yu et al. | 424/642 |
| 5,093,360 | 3/1992 | Yu et al. | 514/463 |
| 5,326,566 | 7/1994 | Parab | 424/401 |
| 5,389,677 | 2/1995 | Yu et al. | 514/557 |
| 5,407,958 | 4/1995 | Heath et al. | 514/546 |
| 5,422,370 | 6/1995 | Yu et al. | 514/557 |
| 5,441,740 | 8/1995 | Ozlen | 424/401 |
| 5,547,988 | 8/1996 | Yu et al. | 514/557 |
| 5,554,597 | 9/1996 | Yu et al. | 514/557 |
| 5,554,652 | 9/1996 | Yu et al. | 514/557 |
| 5,561,157 | 10/1996 | Yu et al. | 514/557 |
| 5,561,158 | 10/1996 | Yu et al. | 514/557 |

*Primary Examiner*—Jyothsna Venkat
*Attorney, Agent, or Firm*—Morton S. Simon

[57] ABSTRACT

The invention provides methods and compositions for improving and reducing age-related skin disorders, particularly fine lines and/or wrinkles, including fine wrinkles, on human skin. The cosmetic compositions of the invention are formulated with less than effective amounts of anti-wrinkle active agents (e.g., drugs) or are devoid of such active agents, which include α-hydroxy acid and derivatives and salts thereof, tretinoin and derivatives and salts thereof, or vitamin C, and which are typically used for treating and reducing skin lines and/or wrinkles. As tested in clinical trials, the compositions of the invention reduced and improved fine lines and/or wrinkles as well as, or better than, preparations containing α-hydroxy acids, α-hydroxy acid salts, tretinoin, or vitamin C, thereby achieving effective anti-wrinkle formulations that are safe, economical and stable, without potential adverse effects to the user that can accompany the use of the aforementioned, typically-employed antiwrinkle preparations and products.

26 Claims, 2 Drawing Sheets

● VEHICLE
■ 30%
△ 21%
▽ 12%

● AMMONIUM LACTATE 30% CREAM
■ AMMONIUM LACTATE 12% CREAM
△ VEHICLE

METHODS AND COMPOSITIONS FOR FINE LINES AND/OR WRINKLES

FIELD OF THE INVENTION

The present invention relates generally to a method for reducing fine lines and/or wrinkles on the skin and to topical compositions employed in such methods. The effacement of facial fine lines and/or wrinkles, as well as other beneficial effects, are achieved by the use of the present invention.

BACKGROUND OF THE INVENTION

A variety of topical treatments are known in the art for mitigating dermatological conditions of the skin which frequently relate to the natural process of aging. Other factors, such as exposure to the sun or the resulting ultraviolet radiation therefrom, improper care and/or diet, stress, nutritional deficiencies, and genetic propensities also contribute to the development of adverse skin conditions, such as fine lines, wrinkles, especially of the facial skin, age spots, keratoses, dry skin, lack of skin tautness and suppleness, and depigmentation.

Many of the compositions described for topical treatment of the skin include components which have adverse side effects to the user, such as drying, burning, stinging, scaling and itching, irritation to the skin, and induction of photosensitivity. Indeed, methods and compositions commonly used for reducing fine lines and/or wrinkles contain acids, particularly, alpha ($\alpha$)-hydroxy acids, such as glycolic acid, lactic acid, tartaric acid and citric acid, and salts thereof, or they contain tretinoin, also known as all-trans retinoic acid or retinol (Vitamin A), or ascorbic acid (Vitamin C), all of which can induce the above-mentioned disadvantageous effects, often due to a lowering of the pH of the skin, among other factors. With particular regard to topical compositions containing tretinoin, medical reports have documented a number of other adverse skin reactions typically associated with their use, namely, burning, tingling, stinging, dryness, peeling, erythema, itching, skin dermatitis, localized swelling and sun sensitivity.

Particular examples of compositions and methods containing retinol or retinoic acid for treating skin conditions and/or reducing wrinkles are found in U.S. Pat. No. 4,826,828 to J. M. Wilmott et al.; U.S. Pat. Nos. 4,603,146, 4,877,805 and 4,888,342 to A. M. Kligman. Particular examples of compositions and methods employing, among other ingredients, various percentages of one or more $\alpha$-hydroxy acids for treating skin conditions and/or reducing wrinkles are found in U.S. Pat. No. 5,547,988 to R. J. Yu et al.; U.S. Pat. No. 5,422,370 to R. J. Yu et al.; U.S. Pat. No. 5,389,677 to R. J. Yu et al.; U.S. Pat. No. 5,407,958 to J. Heath et al.; U.S. Pat. Nos. 5,091,171, 5,093,360, 5,561,158, 5,561,157, 5,554,597 and 5,554,652 to E. J. Van Scott et al.; U.S. Pat. No. 5,441,740 to S. N. Ozlen and U.S. Pat. No. 5,407,958 to J. L. Heath et al.

Methods and compositions containing permeation enhancers for enhancing and/or controlling penetration of topically applied pharmacologically active agents are further known in the art. Specifically, U.S. Pat. No. 5,326,566 to P. V. Parab discloses the use of dibutyl adipate (DBA) and isopropyl myristate (IPM) to increase the skin permeation of an active or drug, for example, $\alpha$-hydroxy acid, or a cosmetically acceptable salt form of $\alpha$-hydroxy acid, and retinoids, after topical application. However, prior to the present invention, those skilled in the art would have had no reason or incentive to employ a permeation enhancer, much less DBA/IPM, in methods and formulations which contain less than effective amounts of the afore-mentioned active agents, or which are devoid of such agents, in the treatment of fine lines and/or wrinkles associated with intrinsic or extrinsic ageing.

U.S. Pat. No. 5,326,566 also discloses vehicle compositions that are similar, but not identical, to the compositions of the present invention. Those having skill in the art are taught from this patent that the disclosed compositions are useful only for the enhanced penetration into the skin of a pharmacologically active agent contained therein. The teachings of this patent do not allow those skilled in the art to learn or appreciate that a vehicle composition containing a less than effective amount of an active agent, or containing no active agent, would have any significant or beneficial effect to the user, particularly, for reducing fine lines and/or wrinkles in the skin.

In contrast to the present invention, pharmacologically active agents that are directed to the problem addressed by the present invention frequently include the use of skin proteins such as collagen and/or elastin, either singly or in combination (see, for example, U.S. Pat. Nos. 3,991,184; 4,179,333; 3,941,722; and German Pat. No. 2,804,024). Other compositions include steroids, such as pregnenolone, in combination with elastin (U.S. Pat. No. 4,474,763).

The present invention was discovered to afford surprising benefits and results in the reduction of fine lines and/or wrinkles, including fine wrinkles, by providing methods and compositions in the absence of, or containing noneffective amounts for such purpose, of the conventionally-used active components of anti-wrinkle compositions and methods, such as the $\alpha$-hydroxy acids, retinoic acid and/or derivatives and salts thereof.

SUMMARY OF THE INVENTION

It is an object of the present invention to provide methods and compositions to effect at least a temporary physiological improvement in the condition of the skin, with the desired goal of a lasting and permanent improvement and enhancement of the condition and quality of the skin. It is a related object of the invention to improve, diminish or alleviate fine lines and/or wrinkles, including fine wrinkles, on the face, especially around the eyes, around the upper and lower lips, and in the smaller area of the cheeks, such fine lines and/or wrinkles being physical signs associated with intrinsic or extrinsic dermatological ageing.

It is yet another object of the invention to provide formulations, i.e., compositions, for improving, reducing or alleviating fine lines and/or wrinkles, including fine wrinkles, associated with intrinsic or extrinsic ageing, wherein the formulations do not require active components, such as retinoids, e.g., retinoic acid or Vitamin A, $\alpha$-hydroxy acids and/or Vitamin C, which may cause detrimental side effects after continued and prolonged use.

The formulations of the present invention comprise, among other components, one or more permeation enhancers, particularly, the combination of DBA/IPM, and, if desired, ingredients to improve the moisturizing properties of the composition after application, thereby enhancing the beneficial effects and sensory comfort of the composition.

It is another object of the present invention to provide improved, safe and inexpensive therapeutic and/or cosmetic compositions for the treatment of various skin conditions, more particularly for the treatment of fine lines and/or wrinkles, including fine wrinkles, of the facial area, without the concomitant skin dryness, scaling, chafing, burning, stinging and irritation and/or other disadvantages that are associated with other types of anti-wrinkle and age-related skin condition treatment compositions and methods.

It is yet another object of the present invention to provide stable, safe, economical and effective cosmetic anti-wrinkle compositions for reducing facial lines, wrinkles, crowsfeet and otherwise enhancing skin quality, and methods employing such compositions.

Further objects and advantages afforded by the present invention will be apparent from the detailed description hereinbelow.

DESCRIPTION OF THE DRAWINGS

The appended drawings of the figures are presented to further describe the present invention and to assist in its understanding through clarification of its various aspects.

DETAILED DESCRIPTION OF THE INVENTION

Figure 1:
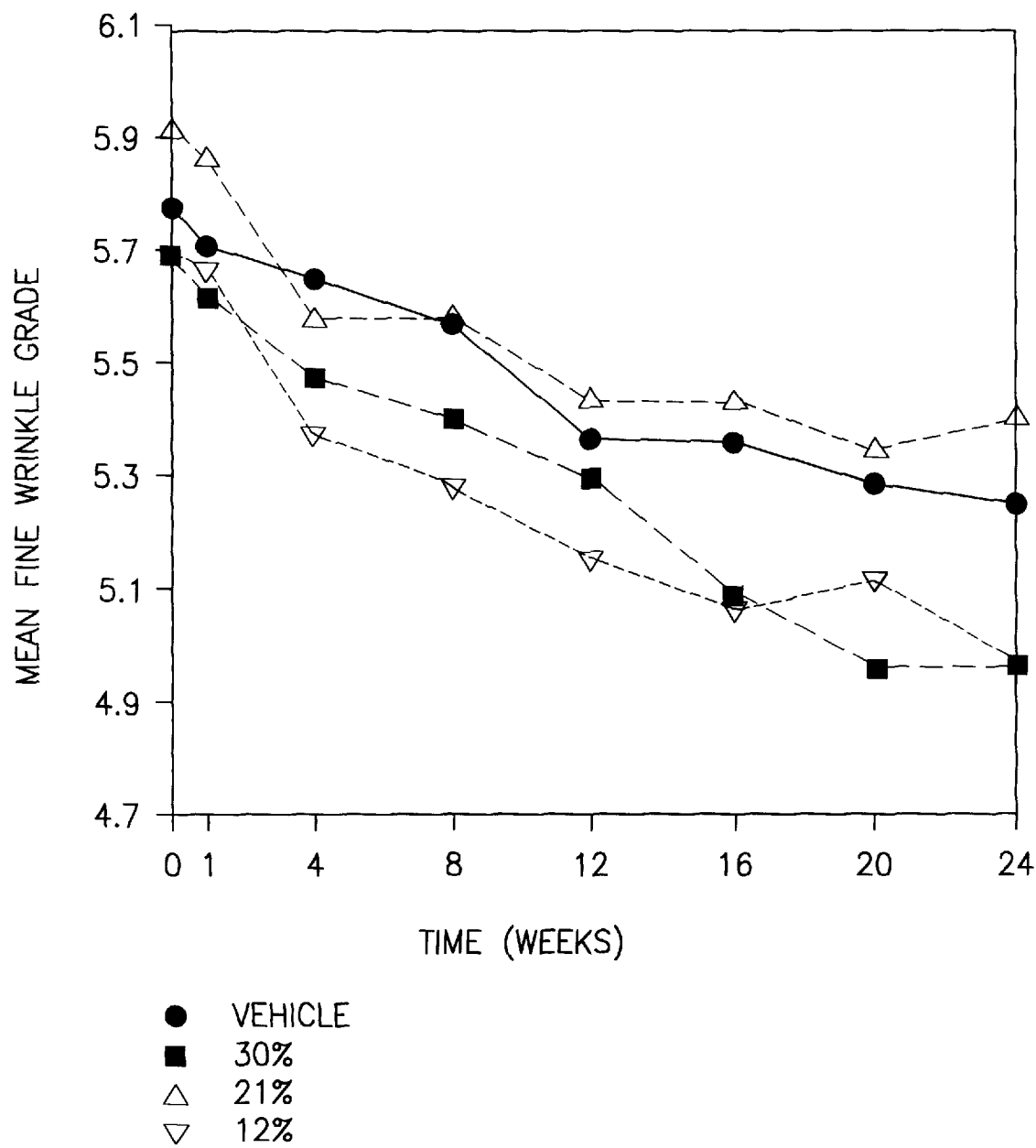
FIG. 1 shows the results of a 24 week clinical study (described in Example 1) performed to evaluate the improvement in facial fine wrinkles after topical application of a cream composition prepared in accordance with the present invention (closed circles), as exemplified in Table 1, compared with cream compositions containing 30% ammonium lactate (closed squares), 21% ammonium lactate (closed upright triangles), or 12% ammonium lactate (closed upside down triangles).

The present invention provides methods and compositions for reducing and/or removing fine lines and/or wrinkles, including fine wrinkles, on the skin via topical application on the desired site. The invention further provides such methods and pharmaceutically acceptable compositions for topical application to human tissues for the purpose of improving the condition of the skin and reducing or alleviating fine lines and/or wrinkles that may be intrinsically or extrinsically provoked.

As mentioned above, the art has typically described the use of retinoic acid and the like, as well as α-hydroxy acids, α-hydroxy acid salts and vitamin C in skin, fine line and/or wrinkle treatment compositions. In addition, the permeation enhancers DBA and IPM have been shown to increase the skin permeation of both α-hydroxy acids and salts thereof in compositions containing these component ingredients (U.S. Pat. No. 5,326,566). However, the present inventor has surprisingly found that a formulation containing DBA/IPM, in the absence of an α-hydroxy acid, or a physiologically acceptable α-hydroxy acid salt, is useful in treating fine lines and/or wrinkles, including fine wrinkles, and crowsfeet, when topically applied to areas of the body, such as the face, neck and hands.

A significant and unexpected finding related to the present invention is that when an α-hydroxy acid or α-hydroxy acid salt was incorporated into the compositions of the present invention, the resulting composition containing these components did not afford any further statistically significant reduction or improvement in fine wrinkles over that afforded by compositions of the present invention which did not contain the α-hydroxy acid or α-hydroxy acid salt. Indeed, the same composition containing no α-hydroxy acid or α-hydroxy acid salt demonstrated a clinically proven effect of marked improvement in fine wrinkles, as further described hereinbelow. Accordingly, the present inventor has unexpectedly discovered that a formulation comprising a physiologically acceptable composition alone (i.e., without a typically-used anti-wrinkle active agent) acted to improve fine lines and/or wrinkles, including fine wrinkles, without the addition of an α-hydroxy acids, or α-hydroxy acid salts, or retinoic acid and related compounds, following topical application on living human skin.

The present invention thus provides compositions comprising a pharmaceutically-acceptable cosmetic formulation which is suitable for contact with living animal tissue, including human tissue, without any adverse physiological effect to the user. Indeed, the compositions of the present invention achieve a surprising diminution and improvement of fine lines and/or wrinkles of the skin in the absence of any pharmacologically active agent (e.g., a drug) that has classically been described and used in the treatment of fine lines and/or wrinkles, and the like, in skin.

The formulations (also called cosmetic compositions) of the present invention include the following essential components: a high level of water, for example, at least about 40%, preferably at least about 60%, more preferably about 70 to 80% by weight, based on the total weight of the composition; one or more permeation enhancers or a combination or mixture thereof; one or more fatty alcohols or mixtures thereof; and an emollient and/or a humectant, preferably a moisturizing humectant, or combinations or mixtures thereof. The formulations may also contain an occlusive agent. A preferred but nonlimiting example of an occlusive agent for use in the formulations of the present invention is mineral oil. As noted hereinbelow, mineral oil can also serve as an emollient in the compositions of the present invention.

As used herein, an emollient refers to a material which deposits an oily film on the surface of the skin, thereby putting an elegant physical barrier on the skin surface to protect the skin from moisture loss. Mineral oil is a nonlimiting example of a suitable emollient for use in the compositions of the present invention. A humectant, or moisturizing humectant, refers to a material which behaves hygroscopically and absorbs moisture from the atmosphere so as to attract moisture to the skin. After application onto the skin, the humectant is absorbed into the skin, leaving only a minimal oily film on the skin surface and providing a smooth feel. Propylene glycol, glycerin and amino acids are nonlimiting examples of suitable humectants for use in the compositions of the present invention.

The compositions of the present invention may be formulated in oil, water, or combinations thereof. Preferred is a dermatologically acceptable formulation comprising an oil-in-water emulsion. Examples of other dermatologically acceptable vehicle formulations of the present invention include, but are not limited to, any suitable non-toxic or pharmaceutically acceptable topical carrier, such as a solution, suspension, emulsion, lotion, ointment, cream, gel, plaster, patch, film, tape or dressing preparation, all of which are well-known to those skilled in the art of topical skin formulations and preparations. Preferred are cream and lotion formulations.

Examples of permeation enhancers suitable for use in the compositions of the present invention include dibutyl adipate, isopropyl myristate and mixtures and/or combinations thereof. Preferred examples of suitable permeation enhancers for use in the compositions of the present invention are dibutyl adipate (DBA) and isopropyl myristate (IPM), or the combination thereof, designated DBA/IPM. The permeation enhancers may be present in the compositions of the invention in an amount of about 0.05% to about 35% by weight, preferably, about 0.2% to about 25% by weight, and more preferably about 2% to about 6% by weight. It is to be understood that, unless specified otherwise, %, by weight, is based on the total weight of the composition.

Examples of fatty alcohols suitable for use in the compositions of the present invention include, but are not limited to, those having from about 4 to about 30 carbon atoms. More specifically, nonlimiting examples of fatty alcohols include stearyl alcohol, cetyl alcohol, cetostearyl alcohol, myristyl alcohol and mixtures or combinations thereof. Preferred are fatty alcohols such as stearyl alcohol and cetyl alcohol. The fatty alcohols can be used in the compositions of the present invention in amounts of about 0.5% to about 15%, preferably about 1% to about 10%, and more preferably about 2% to about 5% by weight.

Examples of emollients suitable for use in the compositions of the present invention include, but are not limited to, dibutyl adipate, diisobutyl adipate, diisopropyl adipate, dimethicone, triglyceride esters of fatty acids such as caprylic/capric triglycerides, hydroxylated lanolin, isopropyl myristate, mineral oil, soya sterol, cetyl stearate and petrolatum and mixtures or combinations thereof. The emollients in the compositions of the present invention are present in the range of about 1% to about 50%, preferably about 2% to about 30%, and more preferably about 3% to about 20% by weight. The preferred emollients are mineral oil, dimethicone, stearyl alcohol, cetyl alcohol, dibutyl adipate, isopropyl myristate and petrolatum.

Emulsifiers can be formulated into the compositions of the present invention. Examples of suitable emulsifiers include, but are not limited to, steareth-2, steareth-21, Tweens®, Spans®, glyceryl monostearate SE (a mixture of glyceryl stearate and PEG-100 stearate) and laureth-4, and mixtures or combinations thereof. The emulsifiers can be present in the compositions in amounts of about 1% to about 12%, preferably about 2% to about 10%, and more preferably, about 3% to about 8% by weight. The preferred emulsifiers for use in the present compositions include steareth-2, steareth-21, glyceryl monostearate SE and laureth-4. It is also to be appreciated that added ingredients such as laureth-4 and the like may also have some permeation enhancing effect when the composition is applied to the skin.

Moisturizing humectants may also be formulated into the compositions of the present invention. Nonlimiting examples of such moisturizing humectants include glycerin, propylene glycol, sorbitol, lactose, mannitol, sodium pyrrolidone carboxylic acid (sodium PCA) and combinations or mixtures thereof. The moisturizing humectants are present in the compositions of the present invention in amounts of about 0.5% to about 15%, preferably about 2% to about 12% and more preferably, about 3% to about 5% by weight. Preferred are glycerin and propylene glycol as humectant moisturizers in the compositions of the present invention.

Other component additives may be formulated into the compositions of the present invention, such as ultraviolet absorbers or sunscreens, antioxidants, preservatives and the like, for enhanced stability during use and storage. Nonlimiting examples of ultraviolet absorbers which may be employed in the formulations of the present invention include octyl dimethyl paraminobenzoic acid (i.e., PABA) and benzophenone-3. Nonlimiting examples of suitable antioxidants and preservatives include, but are not limited to, butylated hydroxytoluene, butylated hydroxyanisole (BHA), sorbic acid, benzoic acid, benzyl alcohol, imidazolidinyl urea, diazolidinyl urea, methylparaben, propylparaben, Kathon CG®, potassium sorbate and mixtures or combinations thereof. The preservatives are present in the compositions of the invention in amounts of about 0.005% to about 2%, preferably about 0.05% to about 1%, and more preferably about 0.1% to about 0.3% by weight. A preferred preservative in the present compositions is sorbic acid.

It is to be understood that the compositions of the present invention may include other conventional topical cosmetic formulation components such as suspending agents, thickeners, film formers, preservatives and fragrant oils. Thickeners are those which are compatible with the overall composition, such as bentones, xanthan gum, fumed silica and ethyl cellulose. Dyes, fragrances and other cosmetic additives may also be present, if desired. In view of the foregoing, the specifically enumerated and exemplified cosmetic components may be freely substituted with other conventional and well known components to achieve a desired texture and lubricity of the compositions, provided that the substitutes do not adversely react with any component of the composition and do not interfere with the homogeneity of the composition.

The composition of the present invention is generally acidic, having a pH in the range of about 2.0 to about 6.8, preferably about 2.5 to about 6, more preferably about 2.8 to about 5.0. The pH is preferably adjusted with sorbic acid. The compositions of the invention may also be formulated in concentrated form and then diluted to produce desired levels of components therein.

The present invention further affords significant advantages to the art; namely, the use of the methods and compositions described herein avoids the need for employing retinoic acid and the side effects that are known to accompany its use. In addition, the invention obviates the use of α-hydroxy acids and α-hydroxy acid salts, which have associated adverse effects, such as possible skin irritation (e.g., dryness, scaling, itching, stinging, burning, erythema and flaking) and possible sensitization to exposure to the sun.

As will be appreciated by those having skill in the art, dibutyl adipate (DBA) and isopropyl myristate (IPM), in combination, have been taught by the present inventor to be a permeation enhancer (U.S. Pat. No. 5,326,566). While not wishing to be bound by any particular theory, a possible mechanism for the action of DBA/IPM in the compositions and methods of the present invention is that the combination causes the permeation of the fatty alcohols, e.g., stearyl alcohol and/or cetyl alcohol, into the skin, thereby helping to retain moisture therein. Without wishing to be bound by a particular theory, the beneficial effect may be heightened by the high level of water contained in the formulation and the occlusive effect of its occlusive agent/emollient components, e.g., mineral oil, etc. This may cause hydration of the skin which serves to mask fine lines and/or wrinkles, to improve skin tone and to assist in the incorporation of the component lipids into the skin after topical application.

The compositions formulated as described herein are topically applied to the skin, generally to the face, to result in an application of about 1 to 4 mg/cm$^2$, preferably about 2 mg/cm$^2$, of skin area, depending on the viscosity of the products. The compositions are generally applied in the areas of the body where fine lines and/or wrinkles are apparent or observed. A moisturizer may be applied concomitantly with or after application of the compositions of the present invention to enhance the tactile comfort associated with application of the composition and to enhance the fine line and/or wrinkle effacement and other benefits achieved by the compositions of the present invention. However, as described, the compositions of the invention may be formulated to contain component ingredients which provide moisturizing properties to the composition as a whole upon application on the skin. In this way, the need for added or separate moisturizers is precluded.

The present invention further encompasses pharmaceutical compositions for topical administration, wherein the compositions are as heretofore described and include a pharmaceutically-acceptable carrier, buffer, diluent or excipient as known to those having skill in the art. Acceptable carriers and the like are those which are compatible with other ingredients in the formulation and which are not deleterious to the user.

In general, it is intended that the compositions of the present invention be applied in an amount and for a time sufficient to effect a reduction of the appearance of a skin fine line and/or wrinkle, including fine wrinkles. It is also intended that the compositions of the present invention be applied to the skin daily. Moreover, application of the compositions to the skin may occur one or more times per day, preferably two times a day, for example, once in the morning and once in the evening. Preferably, the user will not clean the application site for about six hours after application of the composition on the skin.

A course of application of the compositions of the present invention is for a period of at least about four weeks, preferably, for at least about four weeks to about twelve weeks, more preferably, for at least about twelve weeks. Following a course of application (e.g., at least about four to about twelve weeks), fine lines and/or wrinkles, including fine wrinkles, will be reduced and improvement in fine lines and/or wrinkles will be evidenced with minimal to no irritant effects. In addition, application of the product of the present invention will cause neither discomfort nor side effects and skin tone and texture will improve.

EXAMPLES

The examples as set forth herein are meant to exemplify the various aspects of carrying out the present invention and are not intended to limit the invention in any way. Unless otherwise specified, it is to be understood that the concentrations of the component ingredients in the compositions of the present invention are in % by weight (w/w), based on the total weight of the composition.

A number of clinical studies were conducted to evaluate changes in human skin conditions as a result of the topical application of the compositions of the present invention according to the examples herein.

Clinical Studies I and II as illustrated in Examples 1 and 2, respectively, involved at least eighty subjects exhibiting facial photodamage and fine wrinkles. Each treatment group had a parallel group design. Eligible men and women were required to be in an age group of 35 years or older (average age 59 years) with overall severity of signs associated with 1) photodamage of the face greater than or equal to Grade 5 on a scale graded from 0 to 8; and 2) fine wrinkling of the face greater than or equal to Grade 5 on a scale graded from 0 to 8. Subjects applied the product to the face twice a day for 24 weeks. Each subject was evaluated by a Board-certified dermatologist at weeks 0, 1, 4, 8, 12, 16, 20 and 24 or 25 for improvement of fine wrinkles on a scale graded from 0 to 8 as follows:

| Grade Scale For The Improvement Of Fine Wrinkles | |
|---|---|
| Grade | Description of Grade |
| 0 | None (No evidence of fine wrinkles) |
| 1* | |
| 2 | Mild (Mild evidence of fine wrinkles) |
| 3* | |
| 4 | Moderate (Moderate evidence of fine wrinkles) |
| 5* | |
| 6 | Severe (Severe evidence of fine wrinkles) |
| 7* | |
| 8 | Very Severe (Very severe evidence of fine wrinkles) |

*Intermediate intervals (i.e., 1, 3, 5 and 7) are mid-points between the defined grades.

Example 1

The clinical Study I described in this example was designed to test the ability of the compositions of the present invention to reduce and improve the condition of fine wrinkles on facial areas of human test subjects and to compare the efficacy of several different cream compositions. The first composition of the present invention, formulated as a cream in accordance with the invention, comprised the ingredients presented in Table 1. Three other test compositions comprised the ingredients presented Table 1, and also included the ammonium lactate salt of the alpha-hydroxy acid, lactic acid, in amounts of 30%, 21% and 12%, respectively. In essence, the composition of the present invention constitutes a physiologically acceptable cosmetic formulation to which the active agent, e.g., α-hydroxy acid salt, was added.

TABLE 1

| Ingredient | % w/w |
|---|---|
| Propylene glycol | 5.0 |
| Stearyl alcohol | 4.0 |
| Dibutyl adipate | 3.0 |
| Isopropyl myristate | 3.0 |
| Steareth-2 | 2.5 |
| Steareth-21 | 2.5 |
| Magnesium aluminum silicate | 2.0 |
| Dimethicone | 1.0 |
| Laureth-4 | 1.0 |
| Cetyl alcohol | 0.5 |
| Glyceryl monostearate SE | 0.5 |
| Sorbic acid | 0.2 |
| Water | 74.8 |

The results of these comparative studies are shown in FIG. 1. As can be observed from the results shown in FIG. 1, during the course of 24 weeks, the cosmetic composition of the present invention, i.e., a composition in the absence of ammonium lactate as active component (closed circles), surprisingly worked as well at improving and/or reducing facial fine wrinkles as did the composition having 21% ammonium lactate active contained therein.

The change in the grade of fine wrinkles was determined during the course of the 24 week test period. It is numerically represented as a delta (Δ) value (see Table 2). The delta value represents the initial value determined at time 0 minus the value determined at the final measurement timepoint, such as at week 24. As the present inventor unexpectedly discovered, the composition of the instant invention, containing the components presented in Table 1, yielded a delta value (0.56) which was almost identical to that of a composition comprising the active ammonium lactate at a concentration of 21% in the composition (delta value of 0.54).

TABLE 2

| Week | Composition of the Present Invention (No Active) | 30% Ammonium lactate | 21% Ammonium lactate | 12% Ammonium lactate |
|---|---|---|---|---|
| 0 | 5.78 | 5.69 | 5.91 | 5.70 |
| 1 | 5.71 | 5.62 | 5.86 | 5.67 |
| 4 | 5.65 | 5.47 | 5.57 | 5.37 |
| 8 | 5.56 | 5.39 | 5.57 | 5.27 |
| 12 | 5.35 | 5.28 | 5.42 | 5.14 |
| 16 | 5.34 | 5.07 | 5.41 | 5.04 |
| 20 | 5.26 | 4.93 | 5.32 | 5.09 |
| 24 | 5.22 | 4.93 | 5.37 | 4.94 |
| Δ | 0.56 | 0.76 | 0.54 | 0.76 |

In general, the delta value for an active composition should be at least about 1.0. From the data presented in Table 2, it can be observed that the composition of the present invention yielded a delta value of 0.56 versus a delta value of 0.54 for the preparation containing 21% ammonium lactate. Thus, there was no statistically significant difference in delta value between the composition of the present invention and that of the preparation containing the α-hydroxy acid salt, ammonium lactate, at week 24. Moreover, a preparation containing 30% ammonium lactate merely increased the effect demonstrated by the composition of the present invention by an 0.2 delta value, as determined by a comparison of delta values (i.e., 0.76 versus 0.56 in Table 2). In view of the potential adverse effects of the α-hydroxy acids, and salts thereof, for the user, the results from these clinical studies raise the question of why an individual would use a preparation containing α-hydroxy acids or α-hydroxy acid salts if he or she could obtain virtually the same clinical effects with a composition containing no active such as α-hydroxy acids or α-hydroxy acid salts. In sum, it can be determined from the studies presented herein that the presence of adverse active agents in anti-wrinkle compositions does not warrant their use for the treatment of fine lines and/or wrinkles, including fine wrinkles and the like. The compositions afforded by the present invention alleviate detrimental effects to the user due to the mild nature of the product components formulated in the absence of irritants such as the α-hydroxy acids and salts thereof.

Example 2

This example describes a second clinical Study II conducted on human test panelists to determine the effect of the compositions of the present invention on the reduction of fine wrinkles of the face, using a modified cream formulation of the present invention comprising components added to increase the moisturizing capacity of the composition after application on the skin.

Accordingly, the modified composition of the present invention was formulated as a cream and comprised mineral oil and glycerin to enhance moisturization. An illustrative composition containing such moisturizing components is presented in Table 3. The differences between the composition shown in Table 3 and that shown in Table 1 and used in the studies described in Example 1 are that magnesium aluminum silicate (2%) was removed from the former composition and glycerin (3%) and mineral oil (7%) were added. In addition, dibutyl adipate and isopropyl myristate were reduced from 3% to 1%, and propylene glycol was reduced from 5% to 1%, in the composition presented in Table 3.

Two other cream compositions were formulated to include the active ammonium lactate at 30% and 12%, respectively, in a base composition as presented in Table 3. These ammonium lactate-containing compositions were employed in comparative studies, such as those described in Example 1, to determine the effect of the compositions of the present invention versus the effects of the test compositions containing active on the improvement and/or reduction in facial fine wrinkles.

TABLE 3

| Ingredient | % w/w |
|---|---|
| Mineral oil | 7.0 |
| Stearyl alcohol | 4.0 |
| Glycerin | 3.0 |
| Steareth-2 | 2.5 |
| Steareth-21 | 2.5 |
| Dibutyl adipate | 1.0 |
| Isopropyl myristate | 1.0 |
| Dimethicone | 1.0 |
| Laureth-4 | 1.0 |
| Propylene glycol | 1.0 |
| Cetyl alcohol | 0.5 |
| Glyceryl monostearate SE | 0.5 |
| Sorbic acid | 0.2 |
| Water | 74.8 |

Figure 2:
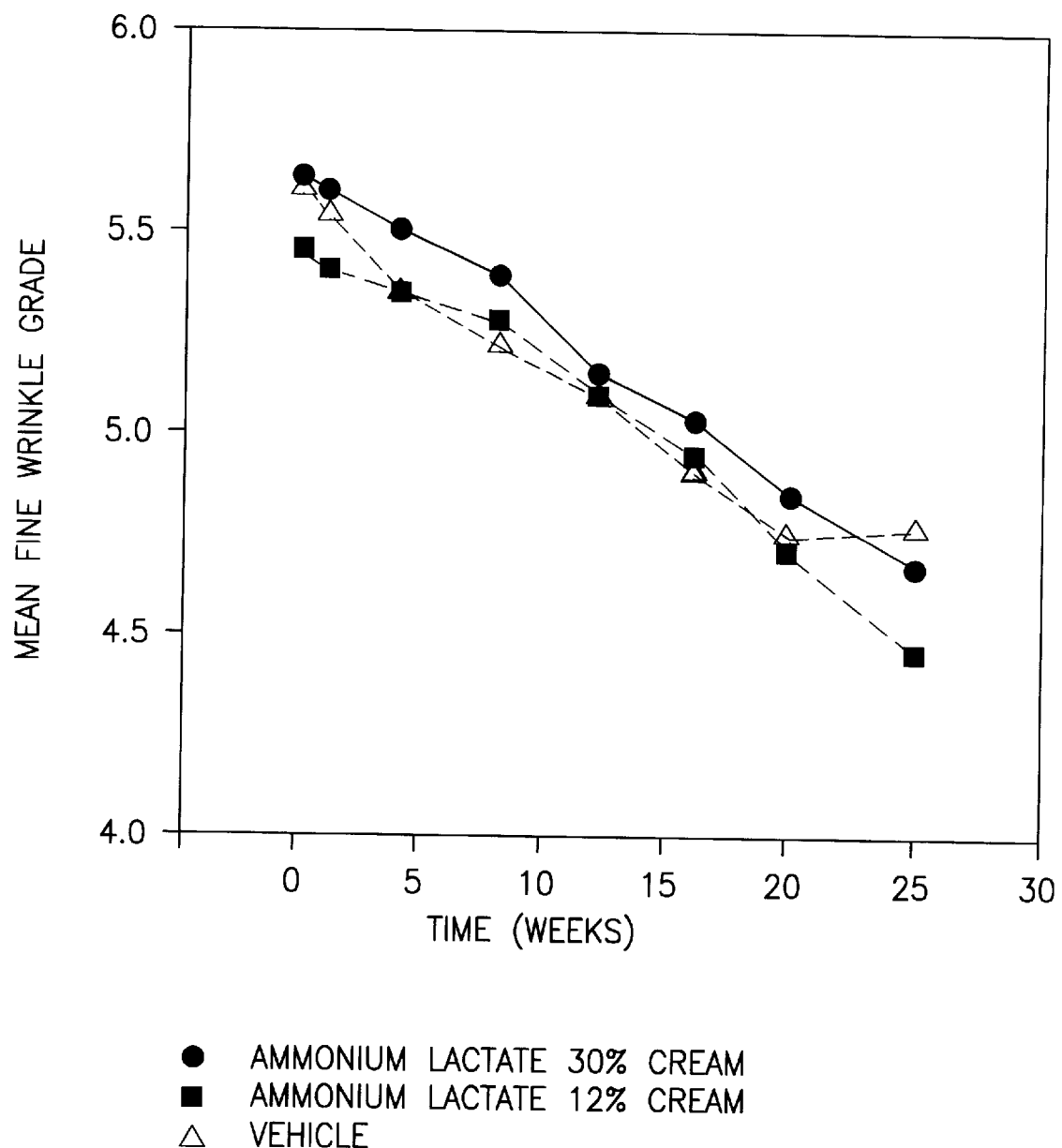
FIG. 2 shows the results of a 25 week clinical study (described in Example 2) carried out to evaluate the improvement in facial fine wrinkles after topical application of a cream composition prepared in accordance with the present invention (closed upright triangles), as exemplified in Table 3, compared with cream compositions containing 30% ammonium lactate (closed circles) or 12% ammonium lactate (closed squares).

The results of the studies described in Example 2 are demonstrated in FIG. 2 and the delta values are presented in Table 4. As graphically shown in FIG. 2, over the 25 week time course of the study, the composition of the present invention containing mineral oil and glycerin (closed triangles) was as effective at improving/reducing fine wrinkles as were the compositions containing 30% ammonium lactate (closed circles) and 12% ammonium lactate (closed squares), respectively. That the present composition, not containing the active α-hydroxy acid salt, improved/reduced facial fine wrinkles at a level that was virtually no different from that of compositions containing the active agent, ammonium lactate, represented a novel and unexpected finding by the present inventor. Thus, the present invention provides a safe, economical and effective means and composition therefor to treat wrinkles and ultimately to reduce fine lines and/or wrinkles, including fine wrinkles, without requiring the use of an active ingredient which is known to have associated deleterious effects to the user.

TABLE 4

| Time (weeks) | 30% Ammonium lactate | 12% Ammonium lactate | Composition of the Present Invention (No Active) |
|---|---|---|---|
| 0 | 5.64 | 5.45 | 5.60 |
| 1 | 5.60 | 5.40 | 5.54 |
| 4 | 5.50 | 5.35 | 5.35 |
| 8 | 5.39 | 5.28 | 5.22 |
| 12 | 5.15 | 5.09 | 5.09 |
| 16 | 5.03 | 4.95 | 4.91 |
| 20 | 4.85 | 4.71 | 4.75 |
| 25 | 4.67 | 4.45 | 4.77 |
| Δ | 0.97 | 1.00 | 0.83 |

As can be seen from the delta values presented in Table 4, there is little difference in these values among the composition of the present invention versus the compositions comprising 30% and 12% active (ammonium lactate) as determined for fine wrinkle improvement/reduction after topical application over the 25 week course of the clinical study. In addition, there was no significant difference between the treatment groups at the end of 25 weeks.

Example 3

Table 5 presents a compilation of the results of studies evaluating the effectiveness on fine wrinkle improvement of formulations comprising 30% and 12% of the active agent, ammonium lactate, versus the composition of the present invention comprising no active ammonium lactate or α-hydroxy acid salt component. Table 5 also presents the results of a Study III describing the effectiveness of a cream containing 0.05% tretinoin (Renova® cream) on the improvement of fine wrinkles compared with the Renova® vehicle containing no active tretinoin. Renova® cream is a commercially available prescription product sold by Ortho Pharmaceutical Corporation (U.S.). The Study III data are reported and described in the Physician's Desk Reference, (PDR), 51st Edition, Medical Consultant: R. Arky, MD, Medical Economics Company, Inc., Montvale, N.J., pp. 1945–1946, 1997).

Renova® emollient cream contains 0.05% tretinoin in a water-in-oil emulsion formulation consisting of light mineral oil, sorbitol solution, hydroxystearate, methoxy PEG-22/dodecyl glycol copolymer, PEG-45/dodecyl glycol copolymer, stearoxytrimethylsilane and stearyl alcohol, dimethicone, fragrance, methylparaben, edetate sodium, quatemium 15, butylated hydroxytoluene, citric acid and water.

According to the PDR publication, the Renova® Study III design consisted of two adequate and well-controlled trials involving 161 evaluable patients treated with vehicle emollient cream on the face for 24 weeks as an adjunct to a comprehensive skin care and sun avoidance program to assess the effectiveness of fine wrinkles and other signs of photodamage. Patients were evaluated at baseline on a 10 point scale and changes from that of the baseline rating were categorized as follows: minimal improvement: reduction of 1 unit; moderate improvement: reduction of 2 units or more. The results of the Renova® Study III, and its comparison to Studies I and II of the present invention, are presented in Table 5.

TABLE 5

Evaluation of Fine Wrinkle Improvement

| Study | Moderate % (Δ > 2) | Mild % (Δ = 1) | Improved % |
| --- | --- | --- | --- |
| I Composition containing 30% ammonium lactate | 15 | 47 | 62 |
| Composition containing 12% ammonium lactate | 15 | 43 | 58 |
| Composition of the Present Invention | 8 | 40 | 48 |
| II Composition containing 30% ammonium lactate | 25 | 26 | 52 |
| Composition containing 12% ammonium lactate | 26 | 32 | 58 |
| Composition of the Present Invention | 29.7 | 31 | 61 |
| III Renova ® Product (0.05% Tretinoin) | 24 | 40 | 64 |
| Renova ® Vehicle | 8 | 30 | 38 |

As indicated by the results presented in Table 5, the Renova® vehicle, formulated in the absence of active tretinoin, provided an about 38% improvement in fine wrinkles, while the Renova® product containing tretinoin active improved fine wrinkles by about 64%.

In Studies I and II, involving compositions comprising the active ammonium lactic acid or lactic acid salt versus the compositions of the present invention containing no α-hydroxy acid salt, the effectiveness of the compositions of the present invention can plainly be observed.

Study I represents a composition containing no ammonium lactic acid or lactic acid salt, no mineral oil and no glycerin, but containing dibutyl adipate and isopropyl myristate, compared with the described compositions containing the active ammonium lactate.

Study II represents a composition of the present invention containing no ammonium lactate, but containing mineral oil and glycerin for added moisturizing properties and dibutyl adipate and isopropyl myristate, compared with the described compositions containing ammonium lactate.

In Study II, the composition of the present invention, containing no ammonium lactate, outperformed the compositions containing either 30% or 12% (w/w) ammonium lactate in improving fine wrinkles, i.e., 61% versus 52% and 58%, respectively. In Study I, the composition of the present invention showed a 48% improvement in fine wrinkles, while the compositions containing ammonium lactate at 30% and 12%, respectively, showed a 62% and a 58% improvement in fine wrinkles.

In accordance with the present invention, these results demonstrate a significant effect on the improvement in fine wrinkles by the compositions of the present invention which are devoid of conventionally-known anti-wrinkle active compounds or drugs, such as α-hydroxy acids, α-hydroxy acid salts, retinoic acid, or Vitamin C. In the particular case of the composition of the present invention containing mineral oil and glycerin, in addition to dibutyl adipate and isopropyl myristate, the performance of the composition of the present invention, without actives, was as good at improving fine wrinkles as the "conventional" compositions containing ammonium lactate in amounts of 30% and 12%. The composition of the present invention was also as good at improving fine wrinkles as the Renova® product which contains the active tretinoin.

These findings demonstrate the surprising and unexpected clinically-proven effects afforded by the compositions of the present invention. The effects were the reduction/improvement in fine wrinkles at a level equal to and even exceeding the levels of conventional anti-wrinkle formulations containing known actives. Moreover, the compositions of the present invention are benign to the health of the user and are devoid of adverse side effects, such as erythema, pruritus, burning, stinging and peeling, that are frequently caused by tretinoin-containing (and α-hydroxy acid-containing) products after topical application. In addition, the compositions of the present invention do not cause photosensitivity to sun or ultraviolet radiation. The compositions of the present invention are also safe and effective for administration to pregnant women and nursing mothers because there is no concern about teratogenic effects associated with their use.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A topical skin composition for reducing the visual appearance of a fine line or wrinkle, said composition containing no active agents having an antiwrinkle effect, said composition consisting essentially of at least about 40by weight, based on the total weight of the composition, of water, about 0.05% to about 35% by weight, based on the total weight of the composition, of one or more permeation enhancing compounds selected from the group consisting of dibutyl adipate, isopropyl myristate, and combinations thereof; about 0.5% to about 15%, by weight based on the total weight of the composition, of one or more fatty alcohols; and one or more emollients or moisturizing humectants and mixtures there of; the emollient being in an amount from about 1 to about 15% by weight, based on the total weight of the composition; the humectant being in an amount of from about 0.5% to about 15% by weight, based on the total weight of the composition; said composition acting to reduce the visual appearance of fine lines or wrinkles.

2. The composition according to claim 1, wherein at least about 60% water is present in the composition.

3. The composition according to claim 1, wherein said fatty alcohol contains from four to thirty carbon atoms, and mixtures or combinations thereof.

4. The composition according to claim 3, wherein said fatty alcohol is selected from the group consisting of stearyl alcohol, cetyl alcohol, myristyl alcohol and mixtures or combinations thereof.

5. The composition according to claim 1, wherein said emollient is selected from the group consisting of, diisopropyl adipate, dimethicone, caprylic triglyceride, capric triglyceride, hydroxylated lanolin, isopropyl myristate, mineral oil, soya sterol, glyceryl stearate, cetyl stearate and petrolatum, and mixtures thereof.

6. The composition according to claim 5, wherein said emollient is selected from the group consisting of mineral oil, dimethicone, stearyl alcohol, cetyl alcohol, glyceryl monostearate, petrolatum and mixtures thereof.

7. The composition according to claim 1, wherein said fatty alcohol is present in said composition in an amount of about 1% to about 10% by weight, based on the weight of the composition.

8. The composition according to claim 1, wherein said emollient is present in said composition in an amount of about 2% to about 30% by weight, based on the weight of the composition.

9. The composition according to claim 1, wherein said humectant is present in said composition in an amount of about 2% to about 12% by weight, based on the weight of the composition.

10. The composition according to claim 1, wherein said moisturizing humectant is selected from the group consisting of glycerin, propylene glycol, sorbitol, lactose, mannitol, sodium pyrrolidone carboxylic acid, and mixtures thereof.

11. The composition according to claim 10, wherein said moisturizing humectant is glycerin or propylene glycol.

12. The composition according to claim 1, wherein said permeation enhancing compounds are present in said composition in an amount of about 0.2% to about 25% by weight, based on the total weight of the composition.

13. The composition according to claim 1, wherein the composition is formulated as an oil-in-water emulsion.

14. The composition according to claim 1, wherein the composition has a pH of about 2.0 to about 6.8.

15. The composition according to claim 1, wherein said permeation enhancing compound is a mixture of dibutyl adipate and isopropyl myristate.

16. The composition according to claim 15, wherein the dibutyl adipate and isopropyl are present in said mixture in a 1:1 ratio.

17. The composition according to claim 15, wherein the composition contains from 1 to 3% dibutyl adipate and from 1 to 3% isopropyl myristate.

18. A method of reducing the visible appearance of a skin fine line or wrinkle, comprising: topically applying to an area of skin containing said line or wrinkle a topical skin composition not containing an effective amount of a drug known to have antiwrinkle effect when topically applied to said fine line or wrinkle, said drug being selected from the group consisting of ammonium lactate and tretinoin; said composition comprising at least about 40% by weight, based on the weight of the composition, of water; about 0.05% to about 35% by weight, based on the weight of the composition, of one or more permeation enhancing compounds selected from the group consisting of dibutyl adipate, isopropyl myristate, and combinations thereof; about 0.5% to about 15% by weight, based on the weight of the composition, of one or more fatty alcohols; and one or more emollients or moisturizing humectants and mixtures thereof; the emollient being in an amount of from about 1 to about 50% by weight, based on the weight of the composition; the humectant being in an amount of from about 0.5% to about 15% by weight, based on the weight of the composition; said composition being applied in an amount and for a time sufficient to effect a reduction of the appearance of said skin line or wrinkle.

19. The method according to claim 18, wherein said composition is applied to the skin for a period of at least about four weeks.

20. The method according to claim 18, wherein said composition is applied to the skin for a period of from at least about four weeks to about twelve weeks.

21. The method according to claim 18, wherein said composition is applied to the skin for a period of at least about twelve weeks.

22. The method according to claim 18, wherein said composition is applied to the skin twice daily.

23. The method according to claim 18, wherein said composition is applied to the skin in an amount of about 1 mg/cm$^2$ to about 4 mg/cm$^2$.

24. The method according to claim 18, wherein said permeation enhancing compounds are a mixture of dibutyl adipate and isopropyl myristate.

25. The method according to claim 24, wherein the dibutyl adipate and isopropyl are present in said mixture in a 1:1 ratio.

26. The method according to claim 24, wherein the composition contains from 1 to 3% dibutyl adipate and from 1 to 3% isopropyl myristate.

* * * * *